United States Patent [19]
Liu et al.

[11] Patent Number: 5,858,986
[45] Date of Patent: Jan. 12, 1999

[54] CRYSTAL FORM I OF CLARITHROMYCIN

[75] Inventors: Jih-Hua Liu, Green Oaks, Ill.; David A. Riley, Kenosha, Wis.; Steven G. Spanton, Green Oaks, Ill.

[73] Assignee: Abbott Laboratories, Abbott Park, Ill.

[21] Appl. No.: 681,723

[22] Filed: Jul. 29, 1996

[51] Int. Cl.$^6$ .............................. A61K 31/70; C07H 1/00; C07H 17/08

[52] U.S. Cl. ........................... 514/29; 536/7.2; 536/18.5; 536/127

[58] Field of Search .......................... 536/7.2, 7.5, 18.5, 536/127; 574/29

[56] References Cited

U.S. PATENT DOCUMENTS

| | | | |
|---|---|---|---|
| 4,670,549 | 6/1987 | Morimoto et al. | 536/7.4 |
| 4,672,109 | 6/1987 | Wantanabe et al. | 536/7.2 |
| 4,990,602 | 2/1991 | Morimoto et al. | |

FOREIGN PATENT DOCUMENTS

97/19096 A  5/1997  WIPO .

OTHER PUBLICATIONS

Quantitative Structure–Activity Relationships In Drug Design, vol. 291 (1989), pp. 325–328, Kim et al., "Conformational Study of Erythromycin Analogues".

Acta Crystallographica, vol. c49, No. 5 (May 1993), pp. 1227–1230, Iwasaki et al., "Structure of 6–O–Methylerythromycin A (Clarithromycin)".

*Primary Examiner*—Elli Peselev
*Attorney, Agent, or Firm*—Mona Anand

[57] ABSTRACT

The present invention concerns the novel antiobiotic 6-O-methylerythromycin A crystal form I, a process for its preparation, pharmaceutical compositions comprising this compound and a method of use as a therapeutic agent.

14 Claims, 6 Drawing Sheets

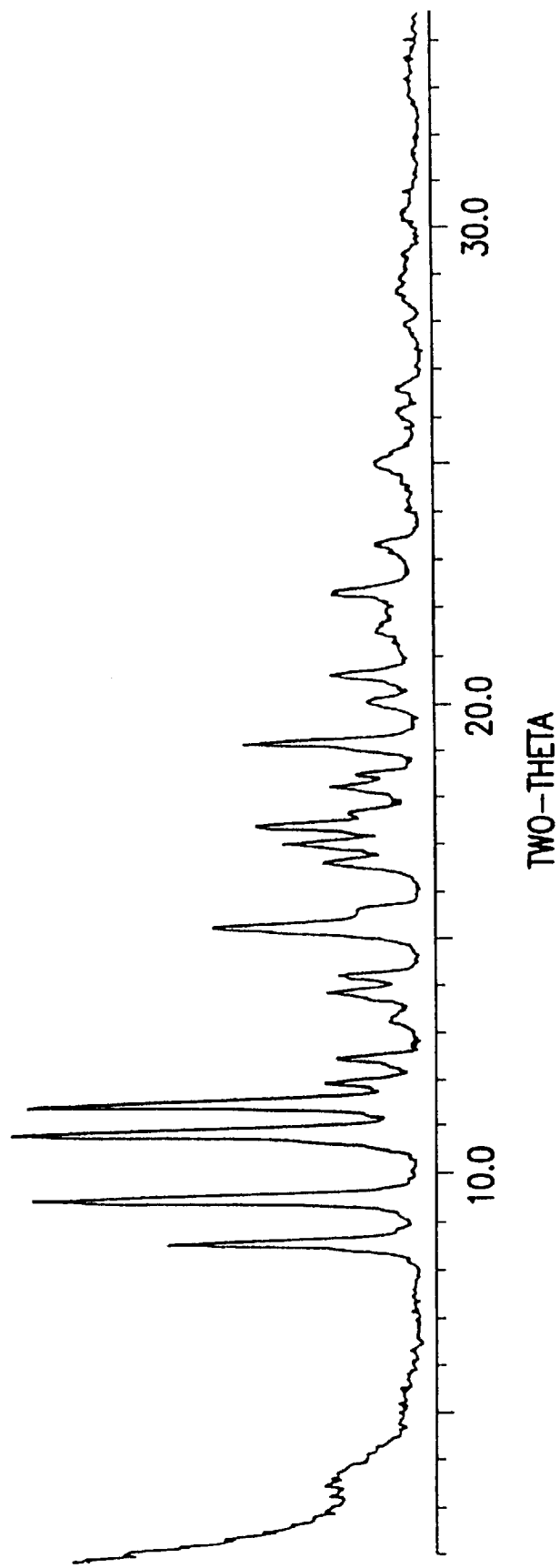

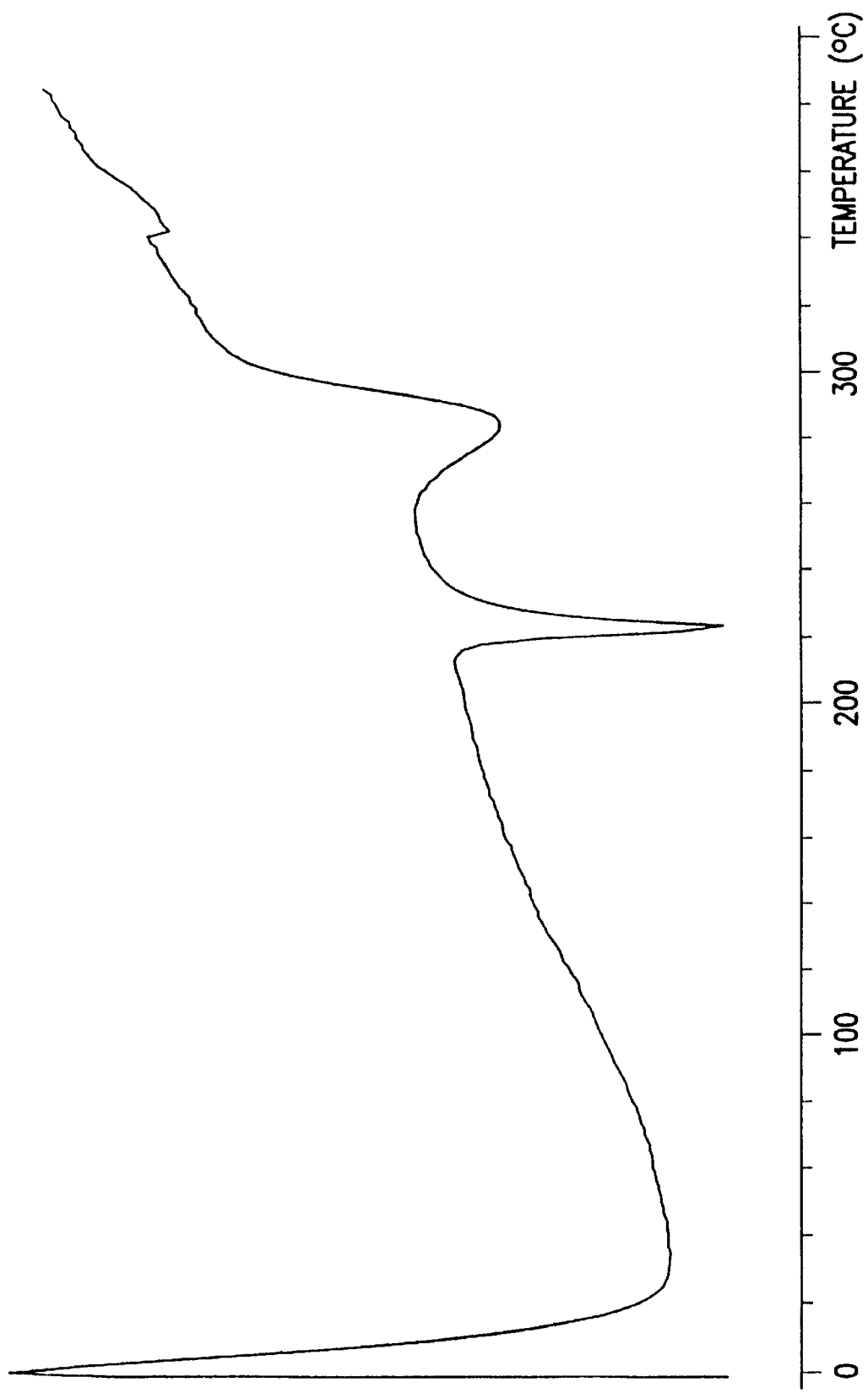

CRYSTAL FORM I OF CLARITHROMYCIN

TECHNICAL FIELD

This invention relates to a compound having therapeutic utility and to a method for its preparation. More particularly, the present invention concerns the novel compound 6-O-methylerythromycin A crystal form I, a process for its preparation, pharmaceutical compositions comprising this compound and a method of use as a therapeutic agent.

BACKGROUND OF THE INVENTION

6-O-methylerythromycin A (Clarithromycin) is a semi-synthetic macrolide antibiotic of formula

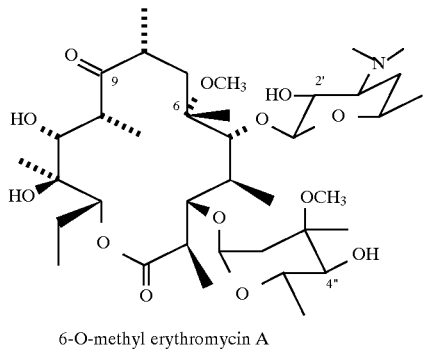

6-O-methyl erythromycin A which exhibits excellent antibacterial activity against gram-positive bacteria, some gram-negative bacteria, anaerobic bacteria, Mycoplasma, and Chlamidia. It is stable under acidic conditions and is efficacious when administered orally. Clarithromycin is a useful therapy for infections of the upper respiratory tract in children and adults.

BRIEF DESCRIPTION OF THE DRAWING

FIGS. 2a, 2b and 2c show, respectively, the powder X-ray diffraction spectrum, the infrared spectrum, and the differential scanning calorimetric (DSC) thermogram of 6-O-methylerythromycin A form II.

SUMMARY OF THE INVENTION

Figure 1A:
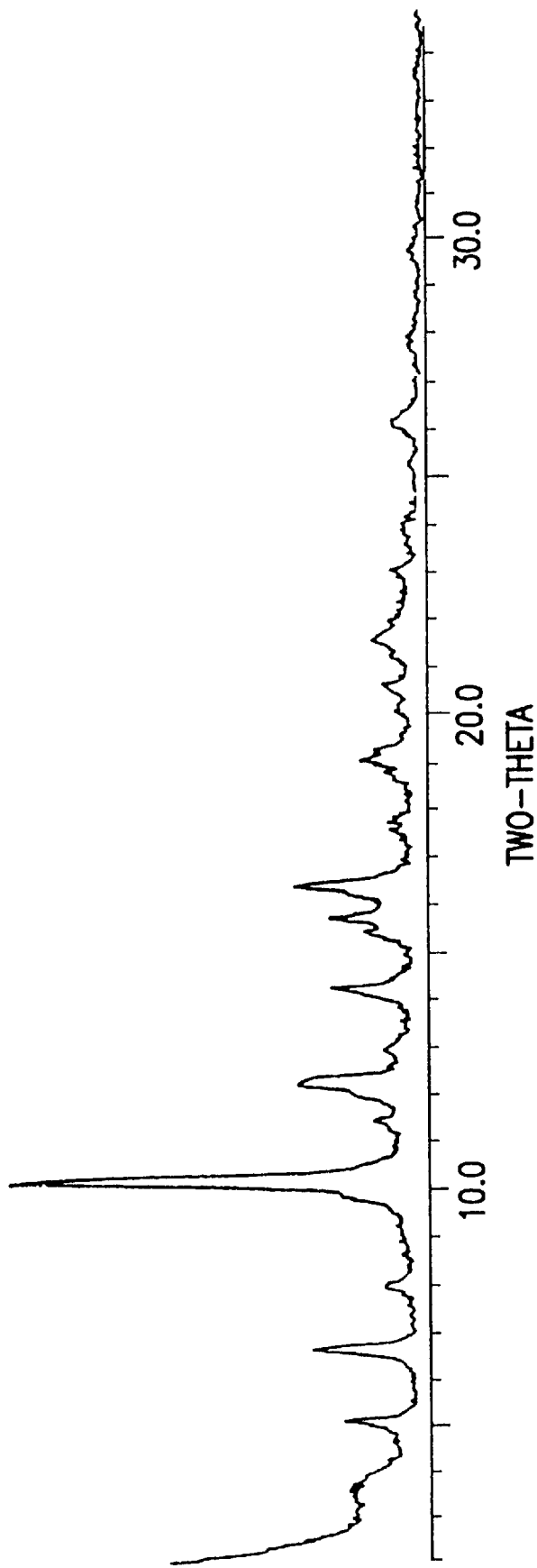
FIGS. 1a, 1b and 1c show, respectively, the powder X-ray diffraction spectrum, the infrared spectrum, and the differential scanning calorimetric (DSC) thermogram of 6-O-methylerythromycin A form I.
Figure 1B:
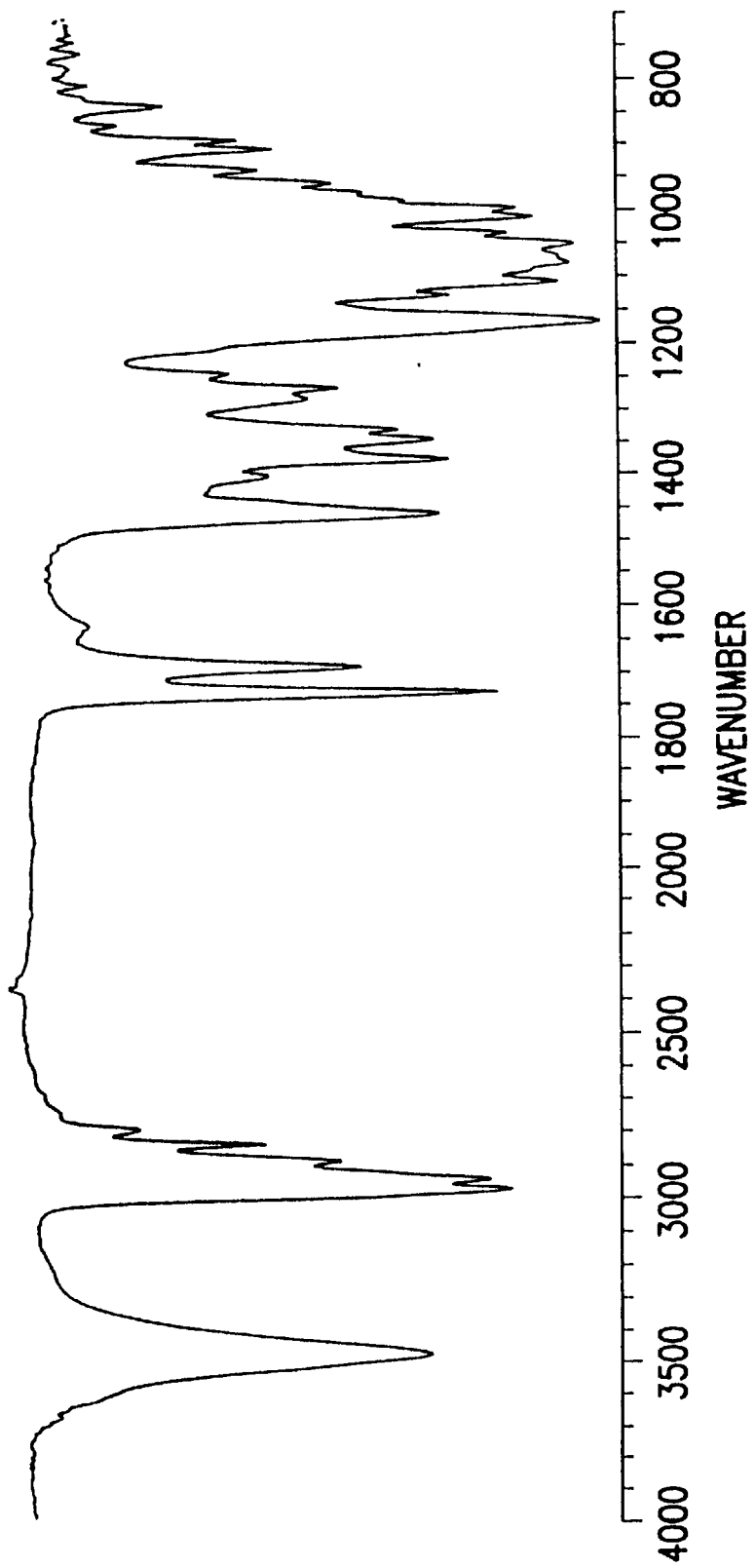
Figure 1C:
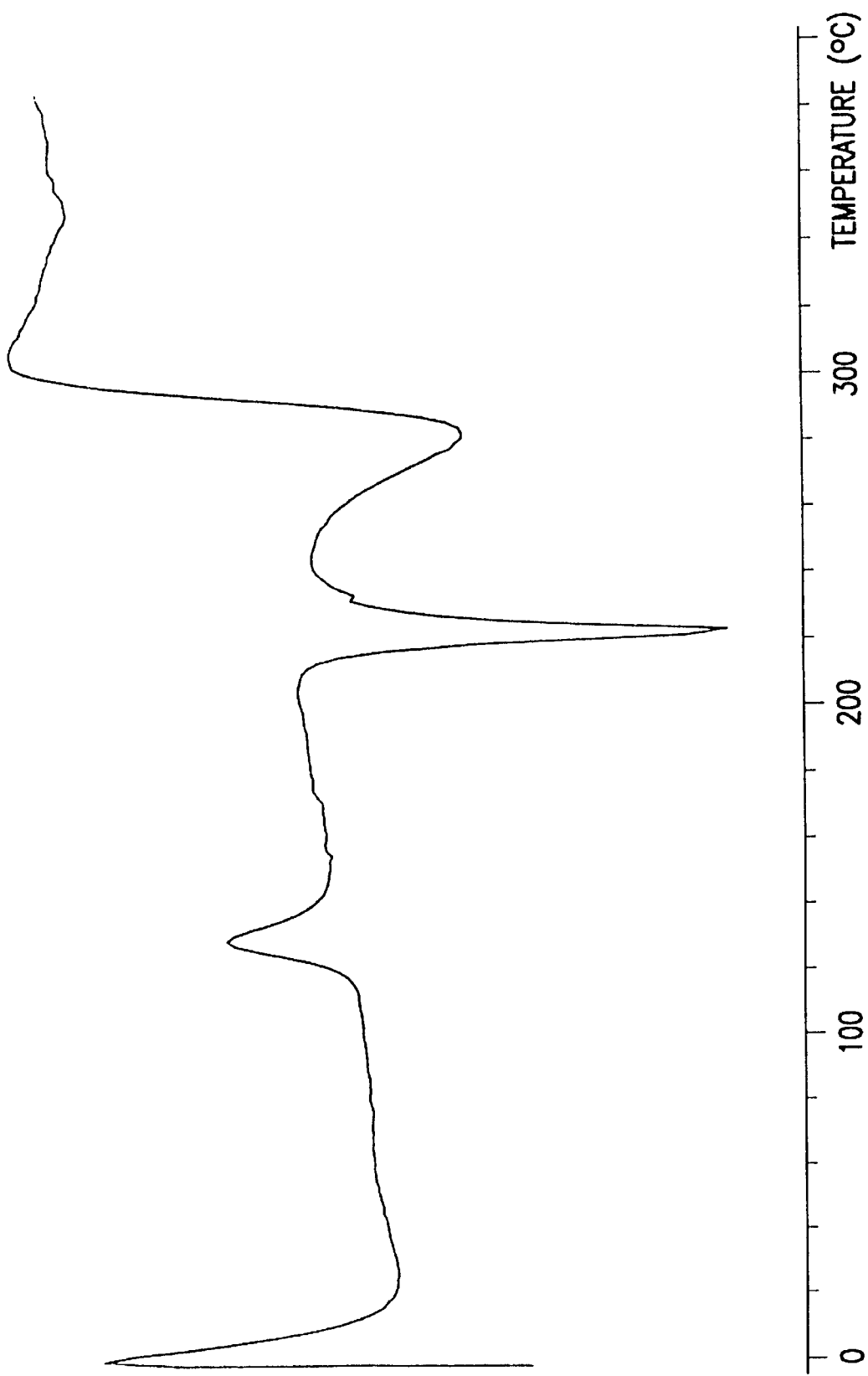
Figure 2B:
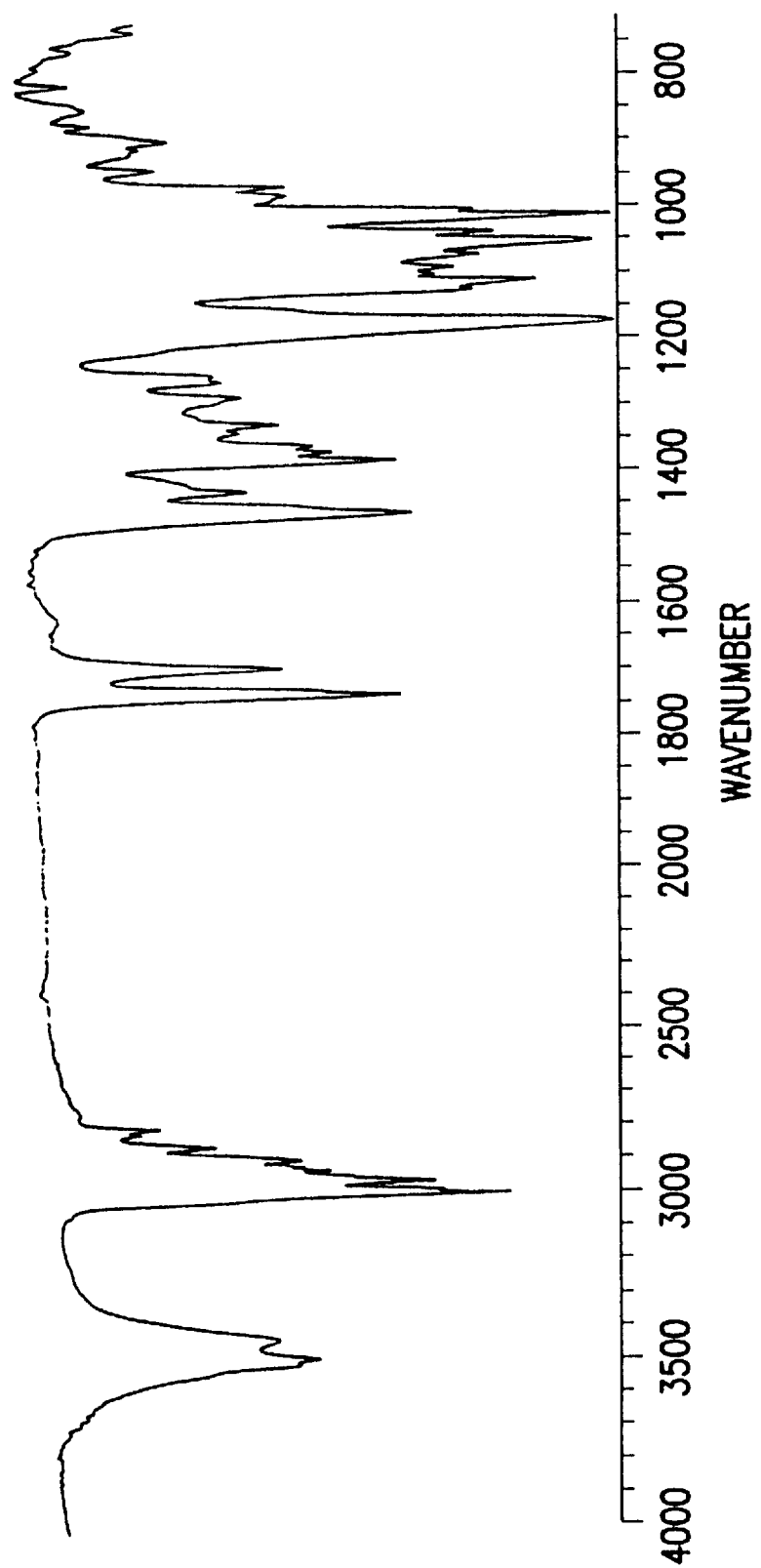

We have discovered that 6-O-methylerythromycin A can exist in at least two distinct crystalline forms, which for the sake of identification are designated "Form I" and "Form II". The crystal forms are identified by their infrared spectrum and powder x-ray diffraction pattern. Form I and form II crystals have an identical spectrum of antibacterial activity, but form I crystals unexpectedly have an intrinsic rate of dissolution about three times that of form II crystals. Investigations in our laboratory have revealed that 6-O-methylerythromycin A prepared by the various methods described in the patent literature summarized below, in which the compound is purified by recrystallization from ethanol, result in exclusive initial formation of crystal form I. Further investigation revealed that recrystallization from tetrahydrofuran, isopropyl acetate, and isopropanol, or mixtures of ethanol, tetrahydrofuran, isopropyl acetate, or isopropanol with other common organic solvents result in exclusive formation of form I crystals.

Drugs currently on the market are formulated from the thermodynamically more stable form II crystals. Therefore, preparation of the current commercial entity requires converting the form I crystals to form II. Typically this is done by heating the form I crystals under vacuum at a temperature of greater than 80° C. Therefore, the discovery of a novel form of 6-O-methylerythromycin A which can be prepared without the high temperature treatment results in substantial processing cost savings. In addition, the favorable dissolution characteristics of form I relative to form II increases bioavailability of the antibiotic and provides significant formulation advantages.

Accordingly, the present invention in its principle embodiment provides a novel crystalline antibiotic designated 6-O-methylerythromycin A form I, or a pharmaceutically acceptable salt thereof.

The present invention also provides pharmaceutical compositions which comprise a therapeutically effective amount of 6-O-methylerythromycin A form I in combination with a pharmaceutically acceptable carrier.

The invention further relates to a method of treating bacterial infections in a host mammal in need of such treatment comprising administering to the mammal a therapeutically effective amount of 6-O-methylerythromycin A form I.

In another embodiment, the present invention provides a process for preparing 6-O-methylerythromycin A form I comprising (a) converting erythromycin A to 6-O- methylerythromycin A;

(b) treating the 6-O-methylerythromycin A with a solvent selected from the group consisting of (i) ethanol, (ii) isopropyl acetate, (iii) isopropanol, (iv) tetrahydrofuran, and (v) a mixture of a first solvent selected from the group consisting of ethanol, isopropyl acetate, isopropanol, and tetrahydrofuran and a second solvent selected from the group consisting of a hydrocarbon of from 5 to 12 carbon atoms, a ketone of from 3 to 12 carbon atoms, a carboxylic ester of from 3 to 12 carbon atoms, an ether of from 4 to 10 carbon atoms, benzene, benzene substituted with one or more substituents selected from the group consisting of alkyl of from one to four carbon atoms, alkoxy of from one to four carbon atoms, nitro, and halogen, and a polar aprotic solvent;

(c) isolating the crystalline 6-O-methylerythromycin A formed in step (b); and (d) drying 6-O-methylerythromycin A isolate in step (c) at a temperature of between ambient temperature and about 70° C. to form 6-O-methylerythromycin A form I.

DETAILED DESCRIPTION

6-O-methylerythromycin A is prepared by methylation of the 6-hydroxy group of erythromycin A. However, in addition to the 6 position, erythromycin A contains hydroxy groups at the 11, 12, 2' and 4" positions, and a nitrogen at 3' position, all of which are potentially reactive with alkylating agents. Therefore, it is necessary to protect the various reactive functionalities prior to alkylation of the 6-hydroxy group. Representative 6-O-methylerythromycin A preparations are described in U.S. Pat. Nos. 4,331,803, 4,670,549, 4,672,109 and 4,990,602 and European Patent Specification 260 938 B1 which are incorporated herein by reference. Following final removal of the protecting groups, the 6-O-methylerythromycin A may exist as a solid, a semisolid, or a syrup containing residual solvents from the deprotection reactions, inorganic salts, and other impurities. 6-O-methylerythromycin A form I may be crystallized directly from the syrup or semisolid using the solvents described above. Alternatively, if the crude reaction product solidifies, the solid may be recrystallized from any of the solvents described above. Pure 6-O-methylerythromycin A form I may also be obtained by recrystallizing form II or mixtures of form I and form II from any of the solvent systems described above. The term "6-O-methylerythromycin A" as used herein is meant to include 6-O-methylerythromycin A Form I or II in any state of purity, or mixtures thereof.

The term "treating" refers to crystallizing or recrystallizing 6-O-methylerythromycin A as defined above from any of the solvents described above.

The term "hydrocarbon" as used herein refers to straight chain or branched alkanes having the formula $C_nH_{2n+2}$. Hydrocarbons useful in the solvent mixtures of the present invention include hexane, heptane, octane and the like.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "ketone" refers to a solvent of formula RC(O)R' where R and R' are straight or branched alkyl. Ketones useful in the solvent mixtures of the present invention include acetone, methyl ethyl ketone, 2-, and 3-pentanone, and the like.

The term "carboxylic ester" means a solvent of formula $RCO_2R'$ where R and R' are straight or branched alkyl. Carboxylic esters useful in the solvent mixtures of the present invention include methyl acetate, ethyl acetate, isobutyl acetate, and the like.

The term "ether" means a solvent of formula ROR' where R and R' are straight or branched alkyl. Ethers useful in the solvent mixtures of the present invention include ethyl ether, diisopropyl ether, methyl tert-butyl ether, and the like.

The term "polar aprotic" refers to solvents which do not contain hydroxy groups but have a relatively high dipole moment. Polar aprotic solvents useful in the solvent mixtures of the present invention include acetonitrile, N,N-dimethylformamide (DMF), dimethyl sulfoxide (DMSO), 1,1-dimethoxyethane (DME), hexamethylphosphoric triamide (HMPA), and the like.

By "pharmaceutically acceptable salt" it is meant those salts which are, within the scope of sound medical judgement, suitable for use in contact with the tissues of humans and lower animals without undue toxicity, imitation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropioniate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. 6-O-methylerythromycin A is prepared from erythromycin A by a variety of synthetic routes. In one method, erythromycin A is converted to 2'-O-3'-N-bis(benzyloxycarbonyl)-N-demethylerythromycin A (I).

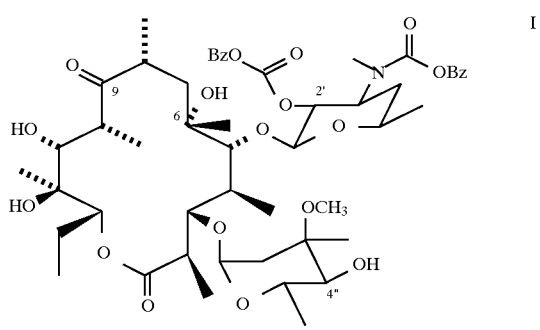

The 6-hydroxy group is then methylated by reaction with an alkylating agent such as bromomethane or iodomethane and a base. Removal of the benzoyl groups by catalytic hydrogenation and reductive methylation of the 3' N gives 6-O-methylerythromycin A. See U.S. Pat. No. 4,331,803.

An alternative synthetic route involves methylation of 6-O-methylerythromycin A-9-oxime. 6-O-methylerythromycin A-9-oxime is prepared by methods well known in the art such as reaction of erythromycin A with hydroxylamine hydrochloride in the presence of base, or by reaction with hydroxylamine in the presence of acid as described in U.S. Pat. No. 5,274,085. Reaction of the oxime with RX wherein R is allyl or benzyl and X is halogen results in formation of 2'-O,3+-N-diallyl or dibenzylerythromycin A-9-O-allyl or benzyloxime halide. Methylation of this quarternary salt as described above, followed by elimination of the R groups and deoximation gives 6-O-methylerythromycin A. See U.S. Pat. No. 4,670,549.

Methylation of 6-O-methylerythromycin A oxime derivatives of formula II,

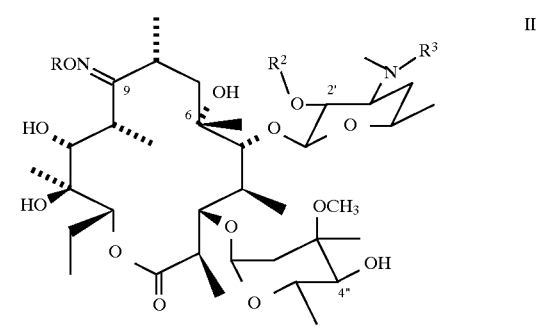

wherein R is alkyl, alkenyl, substituted or unsubstituted benzyl, oxyalkyl, or substituted phenylthioalkyl, $R^2$ is benzoyl, and $R^3$ is methyl or benzoyl, followed by deprotection, deoximation, and reductive methylation when $R^3$ is benzoyl gives 6-O-methylerythromycin A. See U.S. Pat. No. 4,672,109.

A particularly useful preparation of 6-O-methylerythromycin A involves methylation of the oxime derivative III,

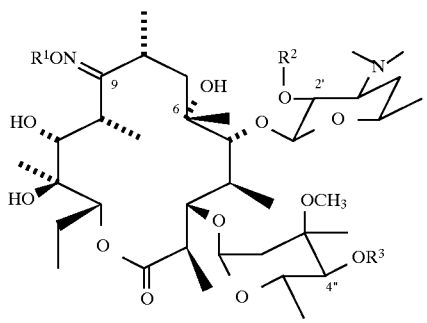

wherein $R^1$ is alkenyl, substituted or unsubstituted benzyl, or alkoxyalkyl, $R^2$ is substituted silyl, and $R^3$ is $R^2$ or H. Removal of the protecting groups and deoximation is then accomplished in a single step by treatment with acid to give 6-O-methylerythromycin A. See European Patent Specification 260 938 B1 and U.S. Pat. No. 4,990,602.

A preferred route ot 6-O-methylerythromycin A is outlined in Scheme 1. Erythromycin A, prepared by fermentation of *Streptomyces erythreus* is oximated to give oxime 4 wherein $R^1$ is alkoxyalkyl. The group $R^1$ may be introduced by reaction of erythromycin A with the substituted hydroxylamine $R^1ONH_2$, or by reaction of erythromycin A with hydroxylamine hydrochloride in the presence of base, or hydroxylamine in the presence of acid, followed by reaction with $R^1X$. The two hydroxy groups are then protected simultaneously, in which $R^2$ or $R^3$ are the same, or sequentially in which $R^2$ and $R^3$ are different. Particularly useful protecting groups are substituted silyl groups such as trimethylsilyl, tert-butyldimethylsilyl, tert-butyldiphenylsilyl and the like. The protecting groups are then removed and the compound is deoximated to produce 6-O-methylerythromycin A. The order of deprotection/deoximation is not critical. When the protecting groups are substituted silyl, deprotection and deoximation can be accomplished in a single step by treatment with acid, for example using formic acid or sodium hydrogen sulfite. See U.S. Pat. No. 4,990,602.

Scheme I

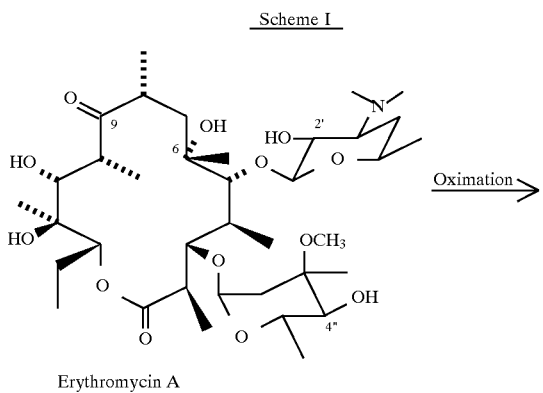

Erythromycin A

-continued
Scheme I

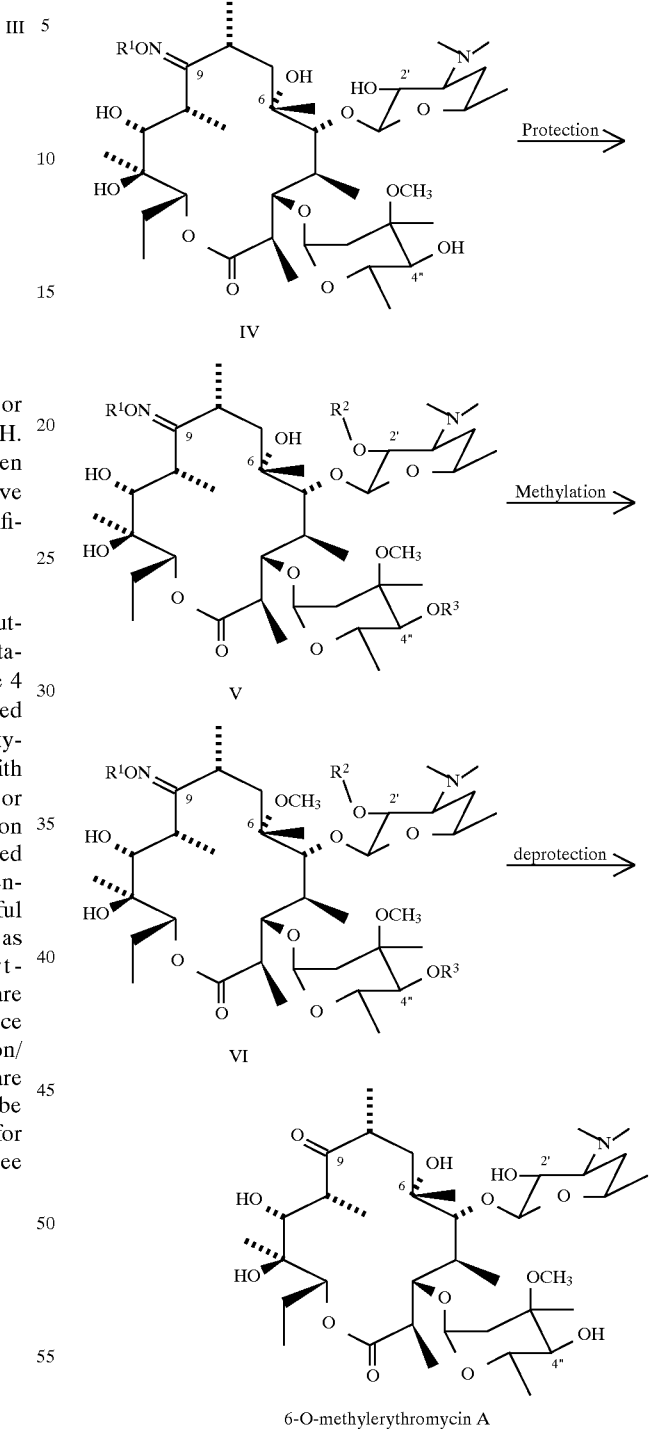

6-O-methylerythromycin A

In accordance with the process aspect of the present invention, 6-O-methylerythromycin A prepared by any of the methods described above is suspended in the desired solvent and heated to about the reflux temperature of the solvent. Heating is then continued and the suspension is stirred for an amount of time sufficient to dissolve most of the solid, generally about 10 minutes to 2 hours. The suspension is then filtered hot. II necessary, the filtrate may be heated to at or about the reflux temperature of the solvent to form a clear solution. The filtrate is then slowly cooled to ambient temperature with optional further cooling in an ice-water bath. For purposes of this specification, ambient temperature is from about 20° C. to about 25° C. Crystalline 6-O-methylerythromycin A is then isolated, preferably by filtration, and the wet solid is converted to 6-O-methylerythromycin A form I by drying in a vacuum oven at a temperature of between ambient temperature and about 70° C., preferably from about 40 to about 50° C. and a pressure of between about 2 inches of mercury and atmospheric pressure to remove any remaining solvent.

In accordance with the aspects of this invention wherein 6-O-methylerythromycin A is recrystallized from solvent mixtures, 6-O-methylerythromycin A is suspended in the first solvent and heated to about the reflux temperature of the solvent. Heating is then continued and the suspension is stirred for an amount of time sufficient to dissolve most of the solid, generally about 10 minutes to 2 hours. The suspension is then filtered hot. The filtrate may be heated to reflux to form a clear solution if necessary. A second solvent is then added to the hot filtrate and the mixture is cooled slowly to ambient temperature with optional further cooling in an ice bath. Representative second solvents include, but are not limited to, hexane, heptane, octane, acetone, methyl ethyl ketone, 2-, and 3-pentanone, methyl acetate, ethyl acetate, isobutyl acetate, ethyl ether, diisopropyl ether, methyl tert-butyl ether, acetonitrile, N,N-dimethylformamide, dimethyl sulfoxide, 1,1-dimethoxyethane, hexamethylphosphoric triamide, benzene, toluene, and chlorobenzene. Hydrocarbons of from 5 to 12 carbon atoms are preferred second solvents. The most preferred second solvent is heptane. After cooling, 6-O-methylerythromycin A crystal form I is isolated by filtration and drying as described above. The amount of second solvent added is dependent on the solubility of the drug in the first solvent and the second solvent, and can be readily determined by one of ordinary skill in the art. Typical ratios fall in the range of about 1:10 to about 2:1 parts by volume of second solvent. A preferred ratio of first solvent to second solvent is 1:1 parts by volume.

Preferred solvents for the isolation of 6-O-methylerythromycin A form I are ethanol, isopropyl acetate, tetrahydrofuran, and isopropanol.

The most preferred solvent for the isolation of 6-O-methylerythromycin A form I is ethanol.

Pharmaceutical Compositions

The present invention also provides pharmaceutical compositions which comprise 6-O-methylerythromycin A form I formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage form for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to from liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 1000, more preferably of about 5 to about 200 mg of 6-O-methylerythromycin A form I per kilogram of body weight per day are administered to a mammalian patient. If desired, the effective daily dose may be divided into multiple doses for purposes of administration, e.g. two to four separate doses per day.

The following Examples are provided to enable one skilled in the art to practice the invention and are merely illustrative of the invention. They should not be read as limiting the scope of the invention as defined in the claims.

EXAMPLE 1

Preparation of 6-O-methylerythromycin Form I

6-O-methylerythromycin A was prepared from erythromycin A by oximation of the C-9 carbonyl, protection of the C-2' and C-4" hydroxy groups, methylation of the C-6 hydroxy group, deoximation and removal of the protecting groups, and recrystallization from ethanol according to the method of U.S. Pat. No. 4,990,602. The material obtained from the recrystallization was dried in a vacuum oven (40°–45° C., 4–8 in. Hg) to give 6-O-methylerythromycin A form I.

In the differential scanning calorimetric thermogram of 6-O-methylerythromycin A form I there can be seen an exothermic transition at 132.2° C. which is believed to be due to a phase transition and an endothermic peak at 223.4° C. which may be due to melting. Another endothermic peak at 283.3° C. followed by an exothermic peak at 306.9° C. may be due to decomposition. After the DSC scan the color of the sample was black. The 2-theta angle positions in the powder x-ray diffraction pattern of 6-O-methylerythromycin A form I are 5.16°±0.2, 6.68°±0.2, 10.20°±0.2, 12.28°±0.2, 14.20°±0.2, 15.40°±0.2, 15.72°±0.2, and 16.36°±0.2.

EXAMPLE 2

Conversion of 6-O-methylerythromycin Form I Crystals to Form II Crystals

6-O-methylerythromycin A form I crystals (0.40 g), prepared as in Example 1, were placed in a vial and heated in the vacuum oven (4–9 in Hg, 100°–110° C.) ()0 C) for 18 hours to give 6-O-methylerythromycin A form II crystals. 6-O-methylerythromycin A form II melts at 223.4° C. In the differential scanning calorimetric thermogram of 6-O-methylerythromycin A form II there can be seen an endothermic peak at 283.3° C. which may be due to decomposition. After the DSC scan the color of the sample was black. The 2-theta angle positions in the powder x-ray diffraction pattern of 6-O-methylerythromycin A form I are 8.52°±0.2, 9.48°±0.2, 10.84°±0.2, 11.48°±0.2, 11.88°±0.2, 12.36°±0.2, 13.72°±0.2, 14.12°±0.2, 15.16°±0.2, 16.48°±0.2, 16.92°±0.2, 17.32°±0.2, 18.08°±0.2, 18.40°±0.2, 19.04°±0.2, 19.88°±0.2, 20.48°±0.2.

EXAMPLE 3

Isolation of 6-O-methylerythromycin Form I by Recrystallization

Recrystallization from Tetrahydrofuran

A mixture of 6-O-methylerythromycin A (20 g), prepared as described in Example 1, in tetrahydrofuran (100 mL) was warmed to reflux and stirred for 15 minutes. The hot solution was filtered to remove traces of insoluble material and cooled to ambient temperature. No crystallization occurred so 10 g of 6-O-methylerythromycin A was added to the solution and the suspension was again heated to reflux, hot filtered, and cooled in an ice bath. The resulting solid was collected by filtration and dried in the vacuum oven (40°–45° C., 4–8 in. Hg) to give 6-O-methylerythromycin A form I (16.74 g).

Recrystallization from isopropyl alcohol

A mixture of 6-O-methylerythromycin A (15 g), prepared as described in Example 1, and isopropyl alcohol (100 mL) was warmed to reflux and heated for 20 minutes. The hot solution was filtered to remove traces of insoluble material. The filtrate was transferred to another flask along with a 50 mL isopropanol rinse, and the solution was again heated to reflux. The clear solution was then cooled slowly to ambient temperature and left standing for seven hours. The resulting solid was collected by filtration and dried in the vacuum oven (40°–45° C., 4–8 in. Hg) to give 6-O-methylerythromycin A form I (13.3 g).

Recrystallization from isopropyl acetate

A mixture of 6-O-methylerythromycin A (10 g), prepared as described in Example 1, and isopropyl acetate (100 mL) was warmed to 73° C. The hot solution was filtered to remove traces of insoluble material. The clear solution was then cooled slowly to ambient temperature. The resulting solid was collected by filtration and dried in the vacuum oven (40°–45° C., 4–8 in. Hg) to give 6-O-methylerythromycin A form I (3.6 g).

Recrystallization from Isopropyl Acetate-Heptane

A mixture of 6-O-methylerythromycin A (10 g), prepared as described in Example 1, and isopropyl acetate (100 mL) was warmed to reflux. A small amount of insoluble material was removed by filtration and the filtrate was transferred to another vessel. The filter flask was rinsed with isopropyl acetate (5 mL) and the filtrate and rinse were combined and heated to reflux. To the resulting clear solution was added heptane (100 mL) and the clear solution was cooled to ambient temperature over 1.5 hours during which time a precipitate formed. The solid was collected by filtration and dried overnight in the vacuum oven (45°–50° C., 4–8 in. Hg) to give 6-O-methylerythromycin A form I (7.0 g).

Recrystallization from Isopropyl Acetate-N,N-dimethylformamide

A mixture of 6-O-methylerythromycin A (12 g), prepared as described in Example 1, and isopropyl acetate (100 mL) was warmed to reflux. A small amount of insoluble material was removed by filtration and the filtrate was transferred to another vessel. The filtrate was heated to reflux and N,N-dimethylformamide (30 mL) was added. The clear solution was cooled to ambient temperature over 1.5 hours during which time a precipitate formed. The solid was collected by filtration and dried overnight in the vacuum oven (49°–50° C., 4–8 in. Hg) to give 6-O-methylerythromycin A form I (6.4 g).

Recrystallization from Tetrahydrofuran-Heptane

To a clear solution of 6-O-methylerythromycin A (10 g), prepared as described in Example 1, in tetrahydrofuran (75 mL) was added heptane (150 mL). The resulting cloudy solution was heated to 71.5° C. at which point it turned clear. The mixture was cooled to ambient temperature over 2 hours, and then was cooled in an ice-water bath for 0.5 hours. The resulting solid was filtered and dried in the vacuum oven (45°–50° C., 3–4 in. Hg) for four days to give 6-O-methylerythromycin A form I (0.50 g).

Recrystallization from Ethanol-Heptane

A mixture of 6-O-methylerythromycin A (10 g), prepared as described in Example 1, and ethanol (100 mL) was warmed to reflux. A small amount of insoluble material was removed by filtration and the filtrate was transferred to another vessel. The filter flask was rinsed with ethanol (20 mL) and the filtrate and rinse were combined and heated at 78° C. until a clear solution was obtained. To die clear solution was added heptane (100 mL) and the clear solution was cooled slowly to ambient temperature and stirred for four days. The resulting solid was collected by filtration and dried in the vacuum oven (45°–50° C., 4–8 in. Hg) to give 6-O-methylerythromycin A form I (4.5 g).

Recrystallization from Isopropanol-Heptane

A mixture of 6-O-methylerythromycin A (4.0 g), prepared as described in Example 1, and isopropanol (50 mL) was warmed to reflux. Heptane (50 mL) was added and the solution was cooled slowly to ambient temperature and then was cooled in an ice-water bath. The resulting solids were collected by filtration and dried in the vacuum oven (4–8 in. Hg) to give 6-O-methylerythromycin A form I (3.6 g).

EXAMPLE 4

Dissolution Rates of 6-O-methylerythromycin Forms I and II

Dissolution studies were carried out at 60 rpm in 300 mL of 0.05M phosphate buffer at 37° C. using a constant surface area ($^{13}/_{32}$" diameter) drug compact. Alliquots were removed periodically and assayed directly by HPLC (5cm×4.6 mm 3μODS-2 "Little Champ" (Regis) column; 50:50 acetonitrile-0.05M pH 4.0 phosphate buffer mobile phase; 1.0 mL/min flow rate). As shown in Table 1, 6-O-methylerythromycin A form I has an intrinsic rate of dissolution about three times greater than form II.

TABLE 1

Intrinsic Dissolution Rates of 6-O-methylerythromycin A forms I and II

| Crystal Form | Dissolution Rate ± S.D. ($\mu$g/min/cm$^2$) |
|---|---|
| I | 636 ± 2.5 |
| II | 203 ± 14 |

The foregoing examples are presented for purposes of illustration and are not intended to limit the scope of the invention. Variations and changes which are obvious to one skilled in the art are intended to be within the scope and nature of the invention as defined in the appended claims.

We claim:

1. A compound having the name 6-O-methylerythromycin A form I exhibiting an exothermic transition at 132.2° C. and characterized by peaks in the powder x-ray diffraction at values of two theta of 5.16°±0.2, 6.68°±0.2, 10.20°±0.2, 12.28°±0.2, 14.20°±0.2, 15.40°±0.2, 15.72°±0.2, and 16.36°±0.2, or a pharmaceutically acceptable salt thereof.

2. A composition comprising a therapeutically effective amount of 6-O-methylerythromycin A form I exhibiting an exothermic transition at 132.2° C. in combination with a pharmaceutically acceptable carrier.

3. A method of treating bacterial infections in a host mammal in need of such treatment comprising administering to the mammal a therapeutically effective amount of 6-O-methylerythromycin A form I exhibiting an exothermic transition at 132.2° C.

4. A process for preparing 6-O-methylerythromycin A form I exhibiting an exothermic transition at 132.2° C. comprising
  (a) converting erythromycin A to 6-O-methylerythromycin A;
  (b) treating the 6-O-methylerythromycin A with a solvent selected from the group consisting of
    (i) ethanol,
    (ii) isopropyl acetate,
    (iii) isopropanol,
    (iv) tetrahydrofuran, and
    (v) a mixture of a first solvent selected from the group consisting of ethanol, isopropyl acetate, isopropanol, and tetrahydrofuran and a second solvent selected from the group consisting of
      a hydrocarbon of from 5 to 12 carbon atoms,
      a ketone of from 3 to 12 carbon atoms,
      a carboxylic ester of from 3 to 12 carbon atoms,
      an ether of from 4 to 10 carbon atoms, benzene,
      benzene substituted with one or more substituents selected from the group consisting of
        alkyl of from one to four carbon atoms,
        alkoxy of from one to four carbon atoms,
        nitro, and
        halogen, and
      a polar aprotic solvent;
  (c) isolating the crystalline 6-O-methylerythromycin A formed in step (b); and
  (d) drying 6-O-methylerythromycin A isolate in step (c) at a temperature of between ambient temperature and about 70° C. to form 6-O-methylerythromycin A form I.

5. The process of claim 4 wherein the 6-O-methylerythromycin A is dried at a temperature of from about 40° C. to about 50° C.

6. The process of claim 4 wherein step (a) comprises
  (i) converting erythromycin A into an erythromycin A 9-oxime derivative;
  (ii) protecting the 2' and 4" hydroxy groups of the erythromycin A 9-oxime derivative prepared in step a;
  (iii) reacting the product of step b with a methylating agent;
  (iv) deprotecting and deoximating the product of step c to form 6-O-methylerythromycin A.

7. The process of claim 6 wherein the 6-O-methylerythromycin A is dried at a temperature of from about 40° C. to about 50° C.

8. A process for preparing 6-O-methylerythromycin A form I according to claim 7 wherein the solvent is selected from the group consisting of
  (a) ethanol,
  (b) isopropyl acetate,
  (c) isopropanol, and
  (d) tetrahydrofuran.

9. A process for preparing 6-O-methylerythromycin A form I according to claim 7 wherein the solvent is ethanol.

10. A process for preparing 6-O-methylerythromycin A form I according to claim 7 wherein the solvent comprises a mixture of a first solvent selected from the group consisting of ethanol, isopropyl acetate, isopropanol, and tetrahydrofuran and a second solvent selected from the group consisting of
  a hydrocarbon of from 5 to 12 carbon atoms,
  a ketone of from 3 to 12 carbon atoms,
  a carboxylic ester of from 3 to 12 carbon atoms,
  an ether of from 4 to 10 carbon atoms, benzene,
  benzene substituted with one or more substituents selected from the group consisting of
    alkyl of from one to four carbon atoms,
    alkoxy of from one to four carbon atoms,
    nitro, and
    halogen, and
  a polar aprotic solvent.

11. A process for preparing 6-O-methylerythromycin A form I according to claim 10 wherein the second solvent is a hydrocarbon from 5 to 12 carbon atoms.

12. A process for preparing 6-O-methylerythromycin A form I according to claim 11 wherein the second solvent is heptane.

13. A process for preparing 6-O-methylerythromycin A form I according to claim 7 wherein the solvent is selected from the group consisting of
  (a) ethanol,
  (b) isopropyl acetate,
  (c) isopropanol,
  (d) tetrahydrofuran,
  (e) isopropyl acetate-heptane,
  (f) isopropyl acetate-N,N-dimethylformamide,
  (g) tetrahydrofuran-heptane,
  (h) ethanol-heptane, and
  (i) isopropanol-heptane.

14. 6-O-methylerythromycin Form I prepared according to the method of claim 7.

* * * * *